United States Patent
Giapis et al.

(10) Patent No.: US 6,924,401 B2
(45) Date of Patent: Aug. 2, 2005

(54) PLASMA MICROJET ARRAYS FOR SELECTIVE OXIDATION OF METHANE TO METHANOL

(75) Inventors: Konstantinos P. Giapis, Pasadena, CA (US); R. Mohan Sankaran, Pasadena, CA (US); Sean McHugh, San Antonio, TX (US)

(73) Assignee: California Institute of Technology, Pasadena, CA (US)

( * ) Notice: Subject to any disclaimer, the term of this patent is extended or adjusted under 35 U.S.C. 154(b) by 140 days.

(21) Appl. No.: 10/645,062

(22) Filed: Aug. 21, 2003

(65) Prior Publication Data

US 2004/0116752 A1 Jun. 17, 2004

Related U.S. Application Data

(63) Continuation-in-part of application No. 10/115,840, filed on Apr. 3, 2002, now Pat. No. 6,700,329.
(60) Provisional application No. 60/405,383, filed on Aug. 23, 2002, and provisional application No. 60/282,949, filed on Apr. 10, 2001.

(51) Int. Cl.[7] .............................................. C07C 27/10
(52) U.S. Cl. ...................... 568/910; 204/169; 204/193; 422/186.21; 422/186.23; 422/186.25
(58) Field of Search .......................... 568/910; 204/169, 204/193; 422/186.21, 186.23, 186.25

(56) References Cited

FOREIGN PATENT DOCUMENTS

JP          10182521 A          12/1996

*Primary Examiner*—Michael L. Shippen
(74) *Attorney, Agent, or Firm*—Daniel L. Dawes; Myers Dawes Andras & Sherman LLP

(57) ABSTRACT

An apparatus and method for converting methane to methanol by partial oxidation comprises a source of methane, a source of oxygen, and a capillary tube having an outflow end and an inflow end communicating with the sources of methane and oxygen. An anode is positioned proximate to but spaced from the capillary tube. A voltage source negatively biases the capillary tube relative to the anode. A plasma jet flows from the outflow end of the capillary tube. The methane partially oxidizes into methanol in a reaction zone in the plasma jet. A collector receives the methanol in the plasma jet for subsequent condensation, separation and purification.

23 Claims, 3 Drawing Sheets

PLASMA MICROJET ARRAYS FOR SELECTIVE OXIDATION OF METHANE TO METHANOL

RELATED APPLICATIONS

The present application is related to U.S. Provisional Patent Application Ser. No. 60/405,383, filed on Aug. 23, 2002, which is incorporated herein by reference and to which priority is claimed pursuant to 35 USC 119. The present application is also a continuation-in-part of U.S. patent application Ser. No. 10/115,840, filed on Apr. 3, 2002, now U.S. Pat. No. 6,700,329 entitled, "Method and Apparatus for Providing Flow-Stabilized Microdischarges in Metal Capillaries, assigned to the same assignee as the present invention, which application in turn claimed priority to U.S. Provisional Patent Application Ser. No. 60/282,949 filed on Apr. 10, 2001, which application and provisional are incorporated herein by reference.

BACKGROUND OF THE INVENTION

1. Field of the Invention

The invention relates to the field of conversion of hydrocarbons by partial oxidation in a gas stream and in particular to the conversion of methane into methanol by partial oxidation.

2. Description of the Prior Art

Methane, a principal component of natural gas, is a major energy source but also a greenhouse gas when uncontrollably emitted. It normal boiling point is −161.5° C., making it expensive to liquefy for ease of storage, transportation and usage. Conversion of methane to methanol would not only solve the aforementioned problems but also address important needs in the chemical and gasoline industries.

Methanol is currently produced from methane in an inefficient and very expensive two step-process involving steam reforming of natural gas to produce syngas which is further converted catalytically into methanol. The direct oxidation of methane to methanol would be much more appealing but there are no commercially viable processes practiced yet. The main problem has been the low yield of methanol, typically 2–3 molar % observed in both homogeneous (gas-phase) and heterogeneous (catalytic) processes.

What is needed is a method for methanol conversion which is not subject to the drawbacks of the prior art.

BRIEF SUMMARY OF THE INVENTION

Low temperature plasma of methane at or about atmospheric pressure in a high molecular oxygen concentration partially oxidizes methane into methanol at molar yields in excess of 11% when the plasma reaction is controlled to be short or stopped at a predetermined time of flight in a plasma flow or distance from the orifice of the plasma microjet. The operational requirements are low and there is no coking apparent over time in the jets.

The invention is a method for converting methane to methanol by partial oxidation comprising the steps of flowing a mixture of methane and oxygen into a capillary tube having an inflow end and an outflow end. The capillary tube is negatively biased relative to an anode. A plasma jet is struck and flows from the outflow end of the capillary tube. The methane is partially oxidized into methanol in the plasma jet in a reaction zone of predetermined length. The methanol in the plasma jet flows past, through or into the anode. The anode as disclosed below may be a hollow aligned tube, a porous screen, or may simply be movable or otherwise shaped to minimize obstruction of the gas flow once the flow starts and the plasma jets are struck. The length of the reaction zone is limited by the cathode-to-anode spacing to optimize partial oxidation of the methane. The method is intended to be performed in normal earth atmosphere at ambient pressures, but may be performed at other pressures and in other gaseous environments, if desired.

The step of flowing a mixture of methane and oxygen into a capillary tube further comprises the steps of mixing the methane and oxygen with an inert carrier and flowing the mixture into the capillary tube.

The step of negatively biasing the capillary tube relative to the anode comprises the step of negatively biasing the capillary tube with a DC voltage.

The step of flowing the methanol in the plasma jet past the anode comprises the step of flowing the methanol into an anode tube aligned with the capillary.

The method further comprises the step of isolating the cathode, reaction zone, and anode in a protective package.

The step of flowing the methanol in the plasma jet past the anode also comprises flowing the methanol through the anode. In the case where the anode is a screen the step of flowing the methanol in the plasma jet past the anode comprises the step of flowing the methanol through the anode screen.

The method further comprises the step of condensing the methanol from the reaction zone.

The method further comprises the step of separating the methanol from other condensed products form the reaction zone.

The method further comprises the step of scaling the method up by flowing a mixture of methane and oxygen into a plurality of capillary tubes, each having an inflow end and an outflow end, negatively biasing the plurality of capillary tube relative to at least one anode, striking a plasma jet flowing from the outflow end of each of the plurality of capillary tubes, partially oxidizing the methane into methanol in the plasma jets in a reaction zone of predetermined length, and flowing the methanol in the plasma jets past the at least one anode.

The invention is also defined as an apparatus for converting methane to methanol by partial oxidation comprising a source of methane and oxygen, a capillary tube having an outflow end and an inflow end communicating with the sources of methane and oxygen, an anode proximate to but spaced from the capillary tube, a voltage source for negatively biasing the capillary tube relative to the anode, a plasma jet flowing from the outflow end of the capillary tube, a reaction zone for partially oxidizing the methane into methanol in the plasma jet, and a collector of the methanol in the plasma jet. The invention is further defined as the apparatus for performing the method described above.

The apparatus includes a plurality of capillary tubes organized into an array of capillary tubes with a corresponding anode.

The apparatus further comprises a plurality of arrays coupled together in serial or parallel topologies.

While the apparatus and method has or will be described for the sake of grammatical fluidity with functional explanations, it is to be expressly understood that the claims, unless expressly formulated under 35 USC 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112. The invention can be better visualized by turning now to the following drawings wherein like elements are referenced by like numerals.

The invention and its various embodiments can now be better understood by turning to the following detailed description of the preferred embodiments which are presented as illustrated examples of the invention defined in the claims. It is expressly understood that the invention as defined by the claims may be broader than the illustrated embodiments described below.

DETAILED DESCRIPTION OF THE PREFERRED EMBODIMENTS

The invention is a homogeneous plasma-assisted microsecond reaction process that permits the direct conversion of methane to methanol at high yields. The nonoptimized methanol yield is an unprecedented 11 molar % efficiency, which is commercially viable. Moreover, by-products include other desirable oxygenates such as ethanol and formaldehyde. The process uses DC plasma microjets that are robust, inexpensive to build, and use little power. It operates at atmospheric pressure which means that no expensive vacuum pumps or compressors are needed. Being a flow device the process is entirely scalable. Since most of the products ($H_2O$, $CH_3OH$, $C_2H_5OH$, $HCOH$) are easily condensable, product fractionization or removal is trivial for further purification.

According to the invention, the process is further: 1) optimized for yield, and 2) adapted to multiple plasma microjet operation. Methanol and other oxygenate yield are increased by careful studies of the available parameter space. A multi tube apparatus demonstrates that the idea is scalable and satisfies questions relating to quantity production.

The invention utilizes a partial oxidation of methane which is the efficient and has high production of active radicals, such as methyl, methylene, oxygen atoms, at low temperatures over a very short reaction zone so that the initial reactions can be quenched before full oxidation. The availability of milli- and micro-second, contact-time reactors could be used for the partial oxidation of higher hydrocarbons (e.g. butane), but these would only fully oxidize methane, probably because of the high temperatures employed for thermal activation. Plasmas, on the other hand, have been very efficient in the production of active radicals at lower gas temperatures and have indeed led to the production of methanol, but at very small yields, typically below 2% molar which is far from economical. The reason for the low yield is the long reaction zones associated with large plasma volumes, even in flow systems.

The use of plasma microjets as efficient generators of radicals partially oxidize methane to methanol at a yield as high as 9% molar at a methane conversion rate of 55% based on uncalibrated gas chromatograph (GC) results. Further optimization will increase these values. The plasma microjets are operated in a flow geometry at high flow rates and at atmospheric conditions.

Figure 1:
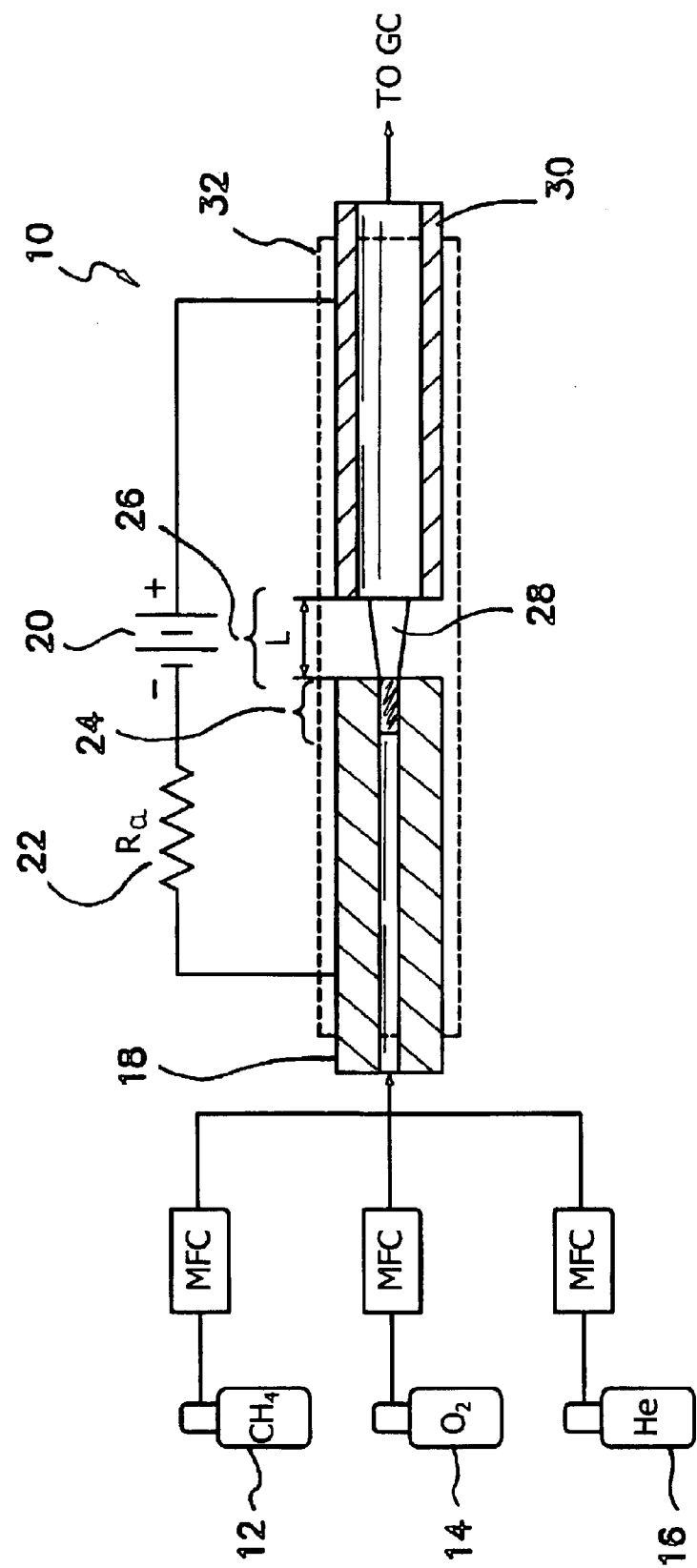
FIG. 1 is a diagram which shows a single microjet used to convert methane to methanol according to the invention.

FIG. 1 is a simplified side cross-sectional diagram of a single plasma microjet 10. In the illustrated embodiment 20 sccm $CH_4$ gas from source 12 and 3.0 sccm $O_2$ gas from source 14 are mixed or combined with a 100 sccm He carrier gas from source 16. The gas mixture is flowed through a conductive or stainless steel tube 18 which has an inner diameter of 178 $\mu$m at room temperature and ambient atmospheric pressures, which tube 18 is operated as the cathode. A DC voltage source 20 providing approximately 7–20 mA at approximately 1000–1500 volts is coupled through a cathode load resistor 22 to negatively biased tube 18 acting as a cathode. A DC micro-hollow cathode discharge is struck in the tube tip section 24 and the plasma jet forms in the outflow region or the reaction zone 26, whose volume or length is important for high conversion rates and discharge stability. In the illustrated embodiment zone 26 is approximately 2–3 mm in length.

It must be understood that all the parameters of operation of microjet 10 are interrelated and can be varied according to the spirit and scope of the invention to empirically optimize partial oxidation of methane in zone 26. Therefore, any one or more of the above described parameters can be altered with compensating alteration in the other parameters in a manner consistent with the teachings of the invention to optimize methane conversion.

A mixture of water and methanol can be condensed out of the effluent 28; the condensate also contains small amounts of ethanol and propanol. The effluent 28 flows into a conductive or stainless steel tube 30 which is positively biased or grounded by voltage source 20 and which acts as the anode. In the illustrated embodiment the inner diameter of tube 30 is 1 mm. Both tubes 18 and 30 are contained within a quartz reactor tube 32, shown in dotted outline, which provides protective isolating packaging for microjet 10. GC analysis of the effluent 28 also indicates that ethane and other higher hydrocarbons are present. The discharge consumes 10 W and can be operated stably for very long times.

Figure 2:
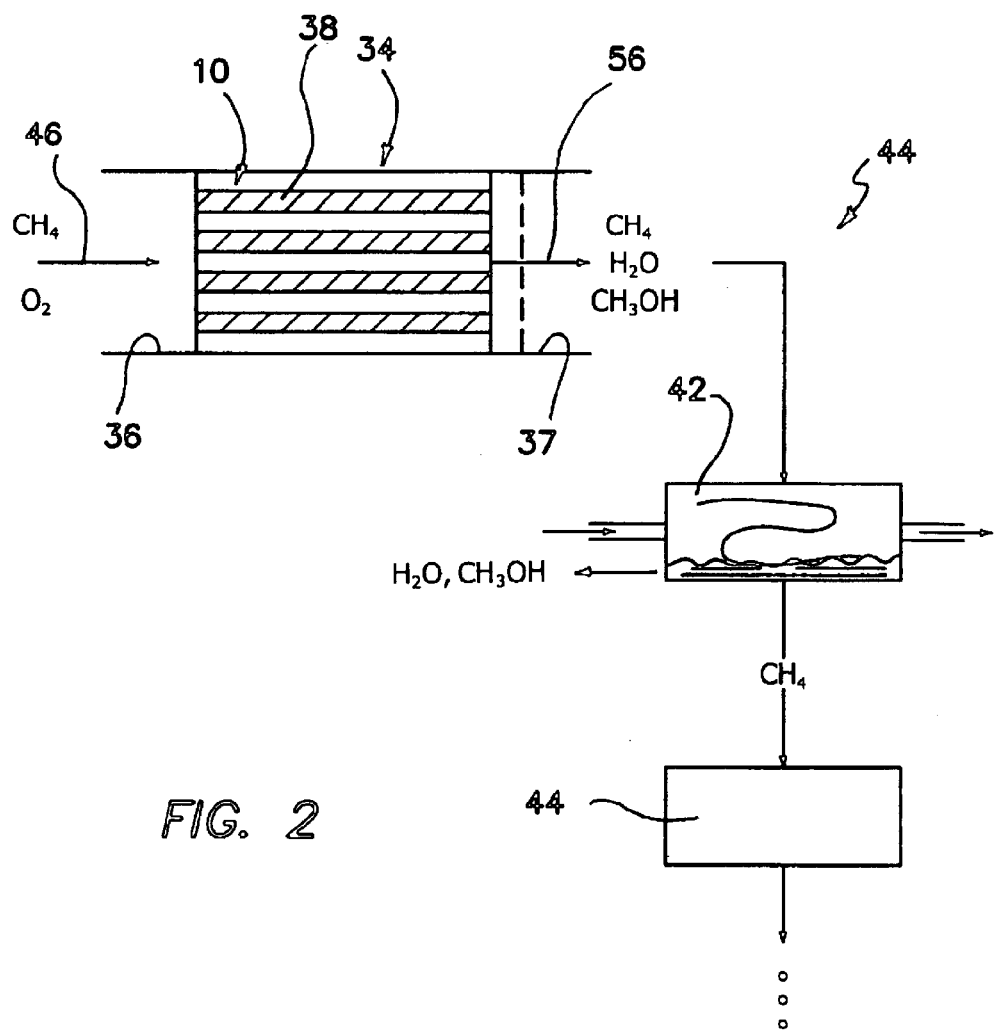
FIG. 2 is a diagram which shows a scaled up production line using the microjets of FIG. 1.

Multiple microjets 10 can be operated in parallel for scaling up operations at higher flow rates for methanol production. FIG. 2 is a simplified diagram of a first embodiment configured for mass production. The input gases of oxygen and methane, and perhaps an inert carrier gas in addition are provided with an intake manifold 36 in an input flow 46. All plurality of microjets 10 of FIG. 1 are arranged in an array 34, which may include a plurality of microjets 10 embedded in or supported by an insulating matrix 38. The gases flow through microjets 10 in array 34, are partially oxidized with an effluent flow 56 of methane, water, methanol and any inert carrier gas used. Flow 56 is then input into a condenser and separator in which all or most of the water, methanol and other possible higher order hydrocarbon products are condensed or liquefied leaving the unoxidized methane and the carrier gas. The water, methanol and other possible higher order hydrocarbon products can then be removed and further purified by conventional chemical manufacturing processes. The array and condenser comprise a converter 44. After one pass through converter 44 the gas products may pass through one or more additional converters 44 with or without further methane enrichment as determined by efficiencies and economies of mass production.

Figure 3:
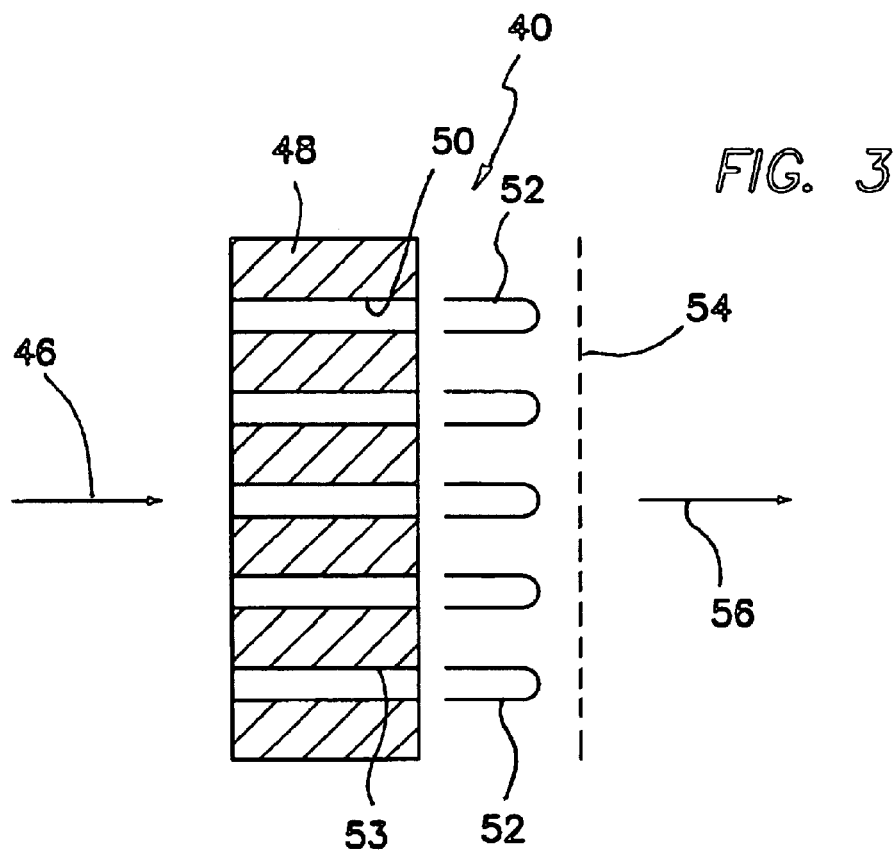
FIG. 3 is a diagram which shows an alternative embodiment of an array of microjets to that shown in FIG. 2.

FIG. 3 is a simplified side cross-sectional view of another embodiment of a microjet array 40. In this example, a plurality of conductive tubes or channels 50 are arrayed in a disk 48. Tubes or channels 50 serve as the cathodes of microjet array 40 and may be comprised of conductive tubes embedded in an insulative material or may be bores defined through a conductive disk or carrier. A gas inflow 46 is provided on one side of the disk 48 with a plurality of plasma jets 52 emerging at the exit orifices 53 on the opposite side of disk 48. An anode screen 54 is disposed opposing exit orifices 53. A gas outflow 56 flows through anode screen 54 and is further processed as described in connection with FIG. 2. Voltage source 20 and load resistor(s) 22 is provided for and coupled to the microjets in a manner similar to that described in connection with FIG. 1.

Figure 4:
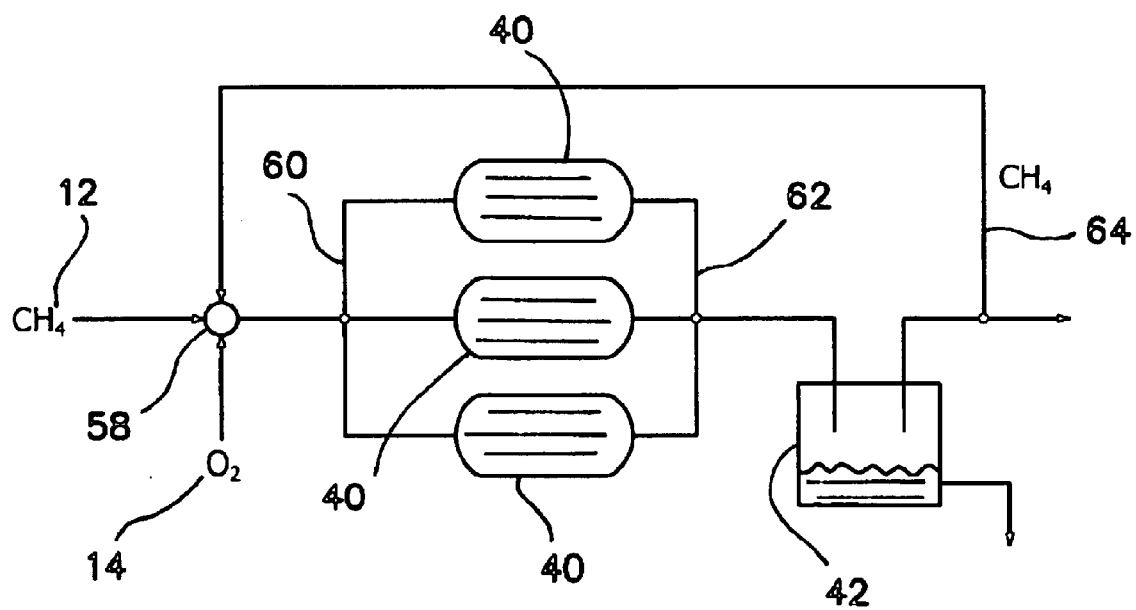
FIG. 4 is diagram which shows a scaled up production line using the microjet arrays of FIG. 3.

FIG. 4 is a simplified diagram of another embodiment where a plurality of microjet arrays 40 are coupled in parallel with each other for mass production. Methane from source 12 is mixed at node 58 with oxygen from source 14 and then provided to a manifold 60, where it is distributed among a plurality of microjet arrays 40. The partially oxidized gas products are collected in parallel in an outflow manifold 62 and then provided to a condenser and separator 42 as in FIG. 2. A portion of the unoxidized methane flowing from condenser and separator 42 is fed back via line 64 to node 58 and recirculated through arrays 40 again. A multiple of such stages as shown in FIG. 4 may be coupled with each other in series with or without methane enrichment at each stage.

In summary, what is described is a method and apparatus to achieve significant partial oxidation of methane, which is cheap, easy to build and operate, scale up and run continuously. Methanol is produced at a high rate, i.e. at least 9%, and can be condense out of the plasma with water for further purification.

Many alterations and modifications may be made by those having ordinary skill in the art without departing from the spirit and scope of the invention. Therefore, it must be understood that the illustrated embodiment has been set forth only for the purposes of example and that it should not be taken as limiting the invention as defined by the following claims. For example, notwithstanding the fact that the elements of a claim are set forth below in a certain combination, it must be expressly understood that the invention includes other combinations of fewer, more or different elements, which are disclosed in above even when not initially claimed in such combinations.

The words used in this specification to describe the invention and its various embodiments are to be understood not only in the sense of their commonly defined meanings, but to include by special definition in this specification structure, material or acts beyond the scope of the commonly defined meanings. Thus if an element can be understood in the context of this specification as including more than one meaning, then its use in a claim must be understood as being generic to all possible meanings supported by the specification and by the word itself.

The definitions of the words or elements of the following claims are, therefore, defined in this specification to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what essentially incorporates the essential idea of the invention.

We claim:

1. A method for converting methane to methanol by partial oxidation comprising:
    flowing a mixture of methane and oxygen into a capillary tube having an inflow end and an outflow end;
    negatively biasing the capillary tube relative to an anode;
    striking a plasma jet flowing from the outflow end of the capillary tube;
    partially oxidizing the methane into methanol in the plasma jet in a reaction zone of predetermined length; and
    flowing the methanol in the plasma jet past the anode.

2. The method of claim 1 where flowing a mixture of methane and oxygen into a capillary tube further comprising mixing the methane and oxygen with an inert carrier and flowing the mixture into the capillary tube.

3. The method of claim 1 where negatively biasing the capillary tube relative to the anode comprising negatively biasing the capillary tube with a DC voltage.

4. The method of claim 1 where flowing the methanol in the plasma jet past the anode comprises flowing the methanol into an anode tube aligned with the capillary.

5. The method of claim 4 further comprising isolating the cathode, reaction zone, and anode in a protective package.

6. The method of claim 1 where flowing the methanol in the plasma jet past the anode comprises flowing the methanol through the anode.

7. The method of claim 1 where the anode is a screen and flowing the methanol in the plasma jet past the anode comprises flowing the methanol through the anode screen.

8. The method of claim 1 further comprising condensing the methanol from the reaction zone.

9. The method of claim 8 further comprising separating the methanol from other condensed products form the reaction zone.

10. The method of claim 1 further comprising scaling the method up by flowing a mixture of methane and oxygen into a plurality of capillary tubes, each having an inflow end and an outflow end, negatively biasing the plurality of capillary tube relative to at least one anode, striking a plasma jet flowing from the outflow end of each of the plurality of capillary tubes, partially oxidizing the methane into methanol in the plasma jets in a reaction zone of predetermined length, and flowing the methanol in the plasma jets past the at least one anode.

11. An apparatus for converting methane to methanol by partial oxidation comprising:

a source of methane;

a source of oxygen;

a capillary tube having an outflow end and an inflow end communicating with the sources of methane and oxygen;

an anode proximate to but spaced from the capillary tube;

a voltage source for negatively biasing the capillary tube relative to the anode;

a plasma jet flowing from the outflow end of the capillary tube;

a reaction zone for partially oxidizing the methane into methanol in the plasma jet; and a collector of the methanol in the plasma jet.

12. The apparatus of claim 11 further comprising a source of an inert carrier and a mixer for mixing the methane and oxygen with the inert carrier and where the mixer communicates with the inflow end of the capillary tube.

13. The apparatus of claim 11 where the voltage source comprises a DC voltage source.

14. The apparatus of claim 11 where the anode comprises an anode tube having an inflow end aligned with the outflow end of the capillary.

15. The apparatus of claim 14 further comprising an isolating protective package enveloping the cathode, reaction zone, and anode.

16. The apparatus of claim 11 where collector comprises an aligned hollow anode arranged and configured to receive the methanol flowing in the plasma jet.

17. The apparatus of claim 11 where the anode is a screen and collector comprises a manifold in which the anode screen is disposed and which is communicated to the outflow end of the capillary tube.

18. The apparatus of claim 11 further comprising a condenser in communication with the collector.

19. The apparatus of claim 18 further comprising a separator for separating the methanol from other condensed products form the reaction zone.

20. The apparatus of claim 11 further comprising a plurality of capillary tubes, each having an inflow end and an outflow end, at least one anode proximate to but spaced from each of the plurality of the capillary tubes, a plurality of plasma jets flowing from the outflow end of each of the plurality of capillary tubes, a reaction zone of predetermined length for partially oxidizing the methane into methanol in each of the plurality of plasma jets, and where the collector collects the methanol form each one of the plurality of plasma jets.

21. The apparatus of claim 20 where the plurality of capillary tubes are organized into an array of capillary tubes with a corresponding anode.

22. The apparatus of claim 21 further comprising a plurality of arrays coupled together in serial or parallel topologies.

23. The apparatus of claim 22 further comprising a condenser in communication with the collectors of each of the plurality of arrays.

* * * * *